(12) United States Patent
Leray et al.

(10) Patent No.: US 8,940,285 B2
(45) Date of Patent: Jan. 27, 2015

(54) SHAMPOO COMPOSITION CONTAINING A CONDITIONING GEL NETWORK

(75) Inventors: Catherine Marie-Joseph Simone Leray, Wirral (GB); Andrew Malcolm Murray, Wirral (GB); Thuy-Anh Pham, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 401 days.

(21) Appl. No.: 13/378,200

(22) PCT Filed: May 27, 2010

(86) PCT No.: PCT/EP2010/057343
§ 371 (c)(1),
(2), (4) Date: Dec. 14, 2011

(87) PCT Pub. No.: WO2010/149460
PCT Pub. Date: Dec. 29, 2010

(65) Prior Publication Data
US 2012/0087883 A1 Apr. 12, 2012

(30) Foreign Application Priority Data
Jun. 24, 2009 (EP) ..................... 09163569

(51) Int. Cl.
| | |
|---|---|
| *A61Q 5/12* | (2006.01) |
| *A61Q 5/02* | (2006.01) |
| *A61K 8/04* | (2006.01) |
| *A61K 8/31* | (2006.01) |
| *A61K 8/37* | (2006.01) |
| *A61K 8/73* | (2006.01) |
| *A61K 8/81* | (2006.01) |

(52) U.S. Cl.
CPC . *A61Q 5/02* (2013.01); *A61K 8/042* (2013.01); *A61K 8/31* (2013.01); *A61K 8/375* (2013.01); *A61K 8/737* (2013.01); *A61K 8/8111* (2013.01); *A61Q 5/12* (2013.01)
USPC ............ 424/70.27; 424/70.1; 424/70.19

(58) Field of Classification Search
CPC ......... A61K 8/042; A61K 8/31; A61K 8/375; A61K 8/8111; A61K 8/737; A61Q 5/02; A61Q 5/12
See application file for complete search history.

(56) References Cited

U.S. PATENT DOCUMENTS

| | | | |
|---|---|---|---|
| 5,892,116 A * | 4/1999 | Weiss et al. ................... | 564/281 |
| 7,303,744 B2 * | 12/2007 | Wells et al. ................ | 424/70.28 |
| 2005/0123487 A1 | 6/2005 | Spadini et al. | |
| 2006/0024256 A1 | 2/2006 | Wells et al. | |
| 2007/0110696 A1 | 5/2007 | Johnson et al. | |

FOREIGN PATENT DOCUMENTS

| | | |
|---|---|---|
| EP | 0584692 A2 | 3/1994 |
| FR | 2262106 A | 9/1975 |
| GB | 1426727 | 3/1976 |
| GB | 2280682 | 8/1995 |
| JP | 2004292387 A | 10/2004 |
| WO | W003101418 A | 12/2003 |
| WO | W02005034895 A | 4/2005 |
| WO | W02007031884 A1 | 3/2007 |
| WO | W02008055815 A | 5/2008 |
| WO | W02008055816 A1 | 5/2008 |
| WO | W02008063471 A2 | 5/2008 |
| WO | W02009072027 A2 | 6/2009 |

OTHER PUBLICATIONS

Co-Pending U.S. Appl. No. 13/378,216, filed Dec. 14, 2011 titled "Concentrated Shampoo".
Co-Pending U.S. Appl. No. 13/378,244, filed Dec. 14, 2011; titled "Antidandruff Shampoo Based on a Gel Network".
PCT international Search Report on Application No. PCT/EP2010/057343, dated Jul. 27, 2011.
Written Opinion on Application No. PCT/EP2010/057343, dated Jul. 27, 2011.
European Search Report on Application No. EP09163569, dated Dec. 11, 2009.
PCT international Search Report on Application No. PCT/EP2010/056335, dated Mar. 21, 2011.
Written Opinion on Application No. PCT/EP2010/056335, dated Mar. 21, 2011.
European Search Report on Application No. EP09163563, dated Nov. 25, 2009.
PCT international Search Report on Application No. PCT/EP2010/056334, dated Dec. 2, 2010.
Written Opinion on Application No. PCT/EP2010/056334, dated Dec. 2, 2010.
European Search Report on Application No. EP09163565, dated Dec. 7, 2009.

* cited by examiner

*Primary Examiner* — Lezah Roberts
*Assistant Examiner* — Nannette Holloman
(74) *Attorney, Agent, or Firm* — Ronald A. Koatz

(57) ABSTRACT

Conditioning shampoo composition with an oil selected from polyalphaolefin oils, ester oils, triglyceride oils, hydrocarbon oils and mixtures thereof dispersed therein, the composition comprising from 1-26% wt. cleansing phase, a conditioning gel network, a polymeric suspending agent and a cationic deposition polymer.

6 Claims, No Drawings

SHAMPOO COMPOSITION CONTAINING A CONDITIONING GEL NETWORK

The present invention relates to a composition comprising an oil.

Despite the prior art there remains a need for improved conditioning shampoo compositions which comprise oils. Improvements are particularly sought with regard to product stability, especially at raised temperatures.

Accordingly, the present invention provides a conditioning shampoo composition according to claim 1.

Preferably, the composition has a viscosity of 2000 to 7000 cPs measures at 30° C., measured on a Brookfield Viscometer using spindle RV5 at 20 rpm.

Preferred oils include those selected from:

Oils having viscosities from 0.1 to 500 centipoises measures at 30 C.

Oils with viscosity above 500 centipoises (500-500000 cps) which contains up to 20% of a lower viscosity fraction (less than 500 cps).

Polyalphaolefin Oil

Preferably, the oil is a polyalphaolefin oil. Polyalphaolefin oils enhance the conditioning benefits found with compositions of the invention.

Suitable polyalphaolefin oils include those derived from 1-alkalene monomers having from 6 to 16 carbons, preferably from 6 to 12 carbons. Non limiting examples of materials include 1-hexene, 1-octene, 1-decene, 1-dodecene, 1-tetradecene, 1-hexadecene, branched isomers such as 4-methyl-1-pentene and mixtures thereof.

Preferred polyalphaloefins include polydecenes with tradename Puresyn 6 having a number average molecular weight of about 500, Puresyn 100 having a molecular weight of about 3000 and Puresyn 300 having a molecular weight of about 6000 commercially available from Mobil.

Preferably, the polyalphaolefin oil is present at from 0.05 to 10%, particularly from 0.2 to 5%, and especially from 0.5 to 3% by weight of the composition.

Triglyceride Oil

Suitable triglyceride oils include fats and oils including natural fats and oils such as jojoba, soybean, sunflower seed oil, rice bran, avocado, almond, olive, sesame, castor, coconut, coconut palm oil, sunflower oil, mink oils; cacao fat; beef tallow, lard; hardened oils obtained by hydrogenating the aforementioned oils; and synthetic mono, di- and triglycerides such as myristic acid glyceride and 2-ethylhexanoic acid glyceride.

Preferably, the triglyceride oil is present at from 0.05 to 10%, particularly from 0.2 to 5%, and especially from 0.5 to 3% by weight of the composition.

Hydrocarbon Oils

Suitable hydrocarbon oils have at least 12 carbon atoms, and include paraffin oil, polyolefin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Preferably, the hydrocarbon oil is present at from 0.05 to 10%, particularly from 0.2 to 5%, and especially from 0.5 to 3% by weight of the composition.

Ester Oils

Suitable ester oils have at least 10 carbon atoms, and include esters with hydrocarbyl chains derived from fatty acids or alcohols. Typical ester oils are formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Preferably, the ester oil is present at from 0.05 to 10%, particularly from 0.2 to 5%, and especially from 0.5 to 3% by weight of the composition.

Preferably, the composition comprises a cleansing anionic surfactant which comprises an alkyl group with from 10 to 14 carbons.

Conditioning Gel Network

Preferably, the conditioning gel network comprises:
(a) fatty material;
(b) a gel network anionic surfactant comprising an alkyl group with from 16 to 30 carbons;
(c) cationic surfactant;
wherein the conditioning gel network has no overall charge or is anionic.

The cationic surfactant provides improved robustness of the fatty material/anionic surfactant gel network leading to improved conditioning benefit from a composition also comprising a non-cationic cleansing phase. The difference in carbon chain length between the anionic surfactant in the cleansing phase and the anionic surfactant in the conditioning gel significantly improve stability of the conditioning gel network and maintain its integrity in the shampoo composition.

Preferably, the anionic and cationic surfactants in the gel network contain within 4, preferably 2 carbons and most preferably the same number of carbons. More preferably, they comprise a single alkyl group of within 4, more preferably within 2 and most preferably are the same length. This assists in maintaining stability of the gel network.

Preferably, the carbons in the gel network cationic surfactant are present in a single alkyl group. More preferably the gel network cationic surfactant has from 16-30 carbons.

Preferably, the cationic surfactants have the formula $N^+(R^1)(R^2)(R^3)(R^4)$, wherein $R^1$, $R^2$, $R^3$ and $R^4$ are independently ($C_{16}$ to $C_{30}$) alkyl or benzyl.

Preferably, one, two or three of $R^1$, $R^2$, $R^3$ and $R^4$ are independently ($C_{16}$ to $C_{30}$) alkyl and the other $R^1$, $R^2$, $R^3$ and $R^4$ group or groups are ($C_1$-$C_6$) alkyl or benzyl.

Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, stearyldimethylbenzylammonium chloride, cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or in admixture with one or more other cationic conditioning surfactants, is a combination of (i) and (ii) below:

(i) an amidoamine corresponding to the general formula (I):

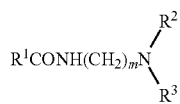

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

The primary role of the acid is to protonate the amidoamine in the hair treatment composition thus forming a tertiary amine salt (TAS) in situ in the hair treatment composition.

The TAS in effect is a non-permanent quaternary ammonium or pseudo-quaternary ammonium cationic surfactant.

Suitably, the acid is included in a sufficient amount to protonate all the amidoamine present, i.e. at a level which is at least equimolar to the amount of amidoamine present in the composition.

The level of cationic surfactant will generally range from 0.01 to 10%, more preferably 0.02 to 7.5%, most preferably 0.05 to 5% by total weight of cationic surfactant based on the total weight of the composition.

The anionic surfactant comprises an alkyl chain with from 16-30 carbons, preferably from 16-22 carbons.

Preferably, the carbons in the gel network anionic surfactant are present in a single alkyl group.

The gel network comprises an anionic surfactant for achieving an overall anionic charge to the gel network or no overall charge to the gel network.

The gel network anionic surfactant is present at from 0.1 to 5% by weight of the composition and more preferably from 0.5 to 2.0% wt.

Preferably, the fatty material is selected from fatty acids, fatty amides, fatty alcohols, fatty esters and mixtures thereof.

Preferably, the fatty material comprises a fatty group having from 14 to 30 carbon atoms, more preferably 16 to 22. Examples of suitable fatty alcohols include cetyl alcohol, stearyl alcohol and mixtures thereof. An example of a suitable fatty ester is glyceryl monostearate.

The level of fatty material in compositions of the invention is conveniently from 0.01 to 10%, preferably from 0.1 to 5% by weight of the composition.

Preferably the ratio between (a) and (b) is from 0.1:1 to 100:1, preferably from 1.2:1 to 50:1, more preferably from 1.5:1 to 10:1 and most preferably around 2:1.

Preferably, the anionic and fatty materials of the gel network contain alkyl groups with within 4, preferably 2 carbons and most preferably the same number of carbons. More preferably, they comprise a single alkyl group of within 4, more preferably within 2 and most preferably are the same length. This assists in maintaining stability of the gel network.

Preferably, the ratio between the gel network anionic surfactant (b) and cationic surfactant (c) is from 6:1 to 20:1, more preferably from 9:1 to 12:1.

Cleansing Phase

The cleaning phase comprises a cleansing surfactant. The cleansing phase anionic surfactant has from 8 to 14 carbons, more preferably from 10 to 12 and most preferably 12 carbons. More preferably, these carbons are present in a single alkyl group.

Preferred anionic cleansing surfactants include alkali metal alkyl sulphates, more preferably the alkyl ether sulphates. Particularly preferred anionic cleansing surfactants include sodium lauryl ether sulphate.

The level of cleansing surfactant is from 5 to 26% by weight of the composition.

Cat Dep Polymer

The composition according to the invention comprises a cationic deposition polymer.

Suitable cationic deposition aid polymers may be homopolymers which are cationically substituted or may be formed from two or more types of monomers. The weight average ($M_w$) molecular weight of the polymers will generally be between 100000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

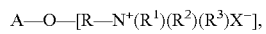

A—O—[R—N⁺(R¹)(R²)(R³)X⁻], wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24.

These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C135, JAGUAR C14, JAGUAR C15 and JAGUAR C17.

Mixtures of any of the above cationic polymers may be used.

Cationic polymer will generally be present in a shampoo composition of the invention at levels of from 0.01 to 5%, preferably from 0.05 to 2%, more preferably from 0.07 to 1.2% by total weight of cationic polymer based on the total weight of the composition.

Preferably, the hair care compositions of the invention are aqueous, i.e. they have water or an aqueous solution or a lyotropic liquid crystalline phase as their major component.

Suitably, the composition will comprise from 10 to 98%, preferably from 30 to 95% water by weight based on the total weight of the composition.

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Water

Preferably, the hair care compositions of the invention are aqueous, i.e. they have water or an aqueous solution or a lyotropic liquid crystalline phase as their major component.

Suitably, the composition will comprise from 10 to 98%, preferably from 30 to 95% water by weight based on the total weight of the composition.

Silicone

The composition according to the invention preferably comprises a silicone.

Particularly preferred silicone conditioning agents are silicone emulsions such as those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. DC7051 is a preferred silicone. These are all emulsions/microemulsions of dimethiconol. Also suitable are amodimethicone emulsions such as DC2-8177 and DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

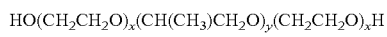

wherein the mean value of x is 4 or more and the mean value of y is 25 or more.

Another preferred form of the surface active block copolymer is according to the following formula:

wherein the mean value of a is 2 or more and the mean value of b is 6 or more.

Mixtures of any of the above described silicone emulsions may also be used.

The above described silicone emulsions will generally be present in a composition of the invention at levels of from 0.05 to 15%, preferably from 0.5 to 12% by total weight of silicone based on the total weight of the composition.

The silicone is preferably present at from 0.5 to 15% wt., more preferably 1 to 12% by weight.

Optionally, a composition of the invention may contain further ingredients as described below to enhance performance and/or consumer acceptability.

Co-Surfactants

The composition can include co-surfactants, to help impart aesthetic, physical or cleansing properties to the composition.

An example of a co-surfactant is a nonionic surfactant, which can be included in an amount ranging from 0.5 to 10%, preferably from 0.7 to 6% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide. A particularly preferred nonionic surfactant is coco mono-ethanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.5 to about 10%, preferably from 1 to 6% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

Suspending Agent

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

The invention will be further illustrated by the following, non-limiting Example, in which all percentages quoted are by weight based on total weight unless otherwise stated.

EXAMPLE

| Component | % ad | Comparative 1 (No gel, No Oil) | Comparative 2 (No Oil, With Gel) | Comparative 3 (No Gel, With Mineral Oil) | Comparative 4 (No Gel, With Polyolefin Oil) |
|---|---|---|---|---|---|
| Sodium Laureth Sulphate | 70 | 17.14 | 17.14 | 17.14 | 17.14 |
| Cocoamidopropyl Betaine | 30 | 5.33 | 5.33 | 5.33 | 5.33 |
| Cocamide MEA | 85 | — | — | — | — |
| Carbomer | 100 | 0.4 | 0.4 | 0.4 | 0.4 |
| Glycol Distearate | 35 | 4.0 | 4.0 | 4.0 | 4.0 |
| Dimethiconol | 50 | 4.0 | 4.0 | 4.0 | 4.0 |
| Sodium Cetylstearyl sulphate | 100 | — | 0.6 | — | — |
| Cetostearyl Alcohol | 100 | — | 1.0 | — | — |
| Behenyl Trimethyl Ammonium Chloride | 77.5 | — | 0.06 | — | — |
| Mineral Oil | 100 | — | — | 0.5 | — |
| Hydrogenated C6-14 Olefin Polymers | 100 | — | — | — | 0.5 |
| Guar Hydroxypropyl Trimonium Chloride | 100 | 0.2 | 0.2 | 0.2 | 0.2 |
| Parfum | 100% | 0.8 | 0.8 | 0.8 | 0.8 |
| DMDM Hydantoin and 3-iodo-2propylnylbutyl carbamate | 50% | 0.2 | 0.2 | 0.2 | 0.2 |
| Sodium chloride | 100% | Visc. | Visc. | Visc. | Visc. |
| Aqua | | q.s. to 100 | q.s. to 100 | q.s. to 100 | q.s. to 100 |

| Component | % ad | Example 1 | Example 2 | Example 3 | Example 4 |
|---|---|---|---|---|---|
| Sodium Laureth Sulphate | 70 | 17.14 | 17.14 | 17.14 | 17.14 |
| Cocoamidopropyl Betaine | 30 | 5.33 | 5.33 | — | — |
| Cocamide MEA | 85 | — | — | 1.0 | 1.0 |
| Carbomer | 100 | 0.4 | 0.4 | 0.4 | 0.4 |
| Glycol Distearate | 35 | 4.0 | 4.0 | 4.0 | 4.0 |
| Dimethiconol | 50 | 4.0 | 4.0 | 4.0 | 4.0 |
| Sodium Cetylstearyl sulphate | 100 | 0.6 | 0.6 | 0.6 | 0.6 |
| Cetostearyl Alcohol | 100 | 1.0 | 1.0 | 1.0 | 1.0 |
| Cetyl trimethyl-ammonium chloride | 29 | — | 0.17 | — | 0.17 |
| Behenyl Trimethyl Ammonium Chloride | 77.5 | 0.06 | — | 0.06 | — |
| Mineral Oil | 100 | 0.5 | 0.5 | 0.5 | 0.5 |
| Guar Hydroxypropyl Trimonium Chloride | 100 | 0.2 | 0.2 | 0.2 | 0.2 |
| Parfum | 100% | 0.8 | 0.8 | 0.8 | 0.8 |
| DMDM Hydantoin and 3-iodo-2propylnylbutyl carbamate | 50% | 0.2 | 0.2 | 0.2 | 0.2 |
| Sodium chloride | 100% | Visc. | Visc. | Visc. | Visc. |

| Component | % ad | Example 1 | Example 2 | Example 3 | Example 4 |
|---|---|---|---|---|---|
| Aqua | | q.s. to 100 | q.s. to 100 | q.s. to 100 | q.s. to 100 |

| BENEFIT Mineral Oil | Comparative 1 | Comparative 2 | Comparative 3 | Example 1 Process1 | Example 1 Process2 |
|---|---|---|---|---|---|
| Softness | 0.5 | 0.47 | 0.51 | 0.72 (95% sign. diff vs Comparative 1) | 0.70 (95% sign. diff vs Comparative 1) |

R-Index Protocol, 18 Panellists

R-index protocol as defined in JOURNAL OF SENSORY STUDIES Volume: 10 Issue: 4 Pages: 341-347 Published: 1995, Author(s): Bi J, O'Mahony M

| Component | % ad | Example 5 | Example 6 | Example 7 | Example 8 |
|---|---|---|---|---|---|
| Sodium Laureth Sulphate | 70 | 17.14 | 17.14 | 17.14 | 17.14 |
| Cocoamidopropyl Betaine | 30 | 5.33 | 5.33 | — | — |
| Cocamide MEA | 85 | — | — | 1.0 | 1.0 |
| Carbomer | 100 | 0.4 | 0.4 | 0.4 | 0.4 |
| Glycol Distearate | 35 | 4.0 | 4.0 | 4.0 | 4.0 |
| Dimethiconol | 50 | 4.0 | 4.0 | 4.0 | 4.0 |
| Sodium Cetylstearyl sulphate | 100 | 0.6 | 0.6 | 0.6 | 0.6 |
| Cetostearyl Alcohol | 100 | 1.0 | 1.0 | 1.0 | 1.0 |
| Cetyl trimethyl-ammonium chloride | 29 | — | 0.17 | — | 0.17 |
| Behenyl Trimethyl Ammonium Chloride | 77.5 | 0.06 | — | 0.06 | — |
| Hydrogenated C6-14 Olefin Polymers | 100 | 0.5 | 0.5 | 0.5 | 0.5 |
| Guar Hydroxypropyl Trimonium Chloride | 100 | 0.2 | 0.2 | 0.2 | 0.2 |
| Parfum | 100% | 0.8 | 0.8 | 0.8 | 0.8 |
| DMDM Hydantoin and 3-iodo-2propylnylbutyl carbamate | 50% | 0.2 | 0.2 | 0.2 | 0.2 |
| Sodium chloride | 100% | Visc. | Visc. | Visc. | Visc. |
| Aqua | | q.s. to 100 | q.s. to 100 | q.s. to 100 | q.s. to 100 |

| BENEFIT | Comparative 1 (No Gel and No Oil) | Comparative 2 (No Oil with Gel) | Comparative 4 (No Gel, With Oil) | Example 5 (With Gel and Oil) |
|---|---|---|---|---|
| Softness | 0.50 | 0.61 | 0.54 | 0.76 (99% sign different compared to Comparative 1) |

R-Index Protocol, 18 Panellists.

| Component | % ad | Example 9 | Example 10 | Example 11 | Example 12 |
|---|---|---|---|---|---|
| Sodium Laureth Sulphate | 70 | 17.14 | 17.14 | 17.14 | 17.14 |
| Cocoamidopropyl Betaine | 30 | 5.33 | 5.33 | — | — |
| Cocamide MEA | 85 | — | — | 1.0 | 1.0 |
| Carbomer | 100 | 0.4 | 0.4 | 0.4 | 0.4 |
| Glycol Distearate | 35 | 4.0 | 4.0 | 4.0 | 4.0 |
| Dimethiconol | 50 | 4.0 | 4.0 | 4.0 | 4.0 |
| Sodium Cetylstearyl sulphate | 100 | 0.6 | 0.6 | 0.6 | 0.6 |
| Cetostearyl Alcohol | 100 | 1.0 | 1.0 | 1.0 | 1.0 |
| Cetyl trimethyl-ammonium chloride | 29 | — | 0.17 | — | 0.17 |
| Behenyl Trimethyl Ammonium Chloride | 77.5 | 0.06 | — | 0.06 | — |
| Trimethylolpropane tricaprylate/tricaprate | 100 | 0.5 | 0.5 | 0.5 | 0.5 |
| Guar Hydroxypropyl Trimonium Chloride | 100 | 0.2 | 0.2 | 0.2 | 0.2 |
| Parfum | 100% | 0.8 | 0.8 | 0.8 | 0.8 |
| DMDM Hydantoin and 3-iodo-2propylnylbutyl carbamate | 50% | 0.2 | 0.2 | 0.2 | 0.2 |
| Sodium chloride | 100% | Visc. | Visc. | Visc. | Visc. |
| Aqua | | q.s. to 100 | q.s. to 100 | q.s. to 100 | q.s. to 100 |

| Component | % ad | Example 13 | Example 14 | Example 15 | Example 16 |
|---|---|---|---|---|---|
| Sodium Laureth Sulphate | 70 | 17.14 | 17.14 | 17.14 | 17.14 |
| Cocoamidopropyl Betaine | 30 | 5.33 | 5.33 | — | — |
| Cocamide MEA | 85 | — | — | 1.0 | 1.0 |
| Carbomer | 100 | 0.4 | 0.4 | 0.4 | 0.4 |
| Glycol Distearate | 35 | 4.0 | 4.0 | 4.0 | 4.0 |
| Dimethiconol | 50 | 4.0 | 4.0 | 4.0 | 4.0 |
| Sodium Cetylstearyl sulphate | 100 | 0.6 | 0.6 | 0.6 | 0.6 |
| Cetostearyl Alcohol | 100 | 1.0 | 1.0 | 1.0 | 1.0 |
| Cetyl trimethyl-ammonium chloride | 29 | — | 0.17 | — | 0.17 |
| Behenyl Trimethyl Ammonium Chloride | 77.5 | 0.06 | — | 0.06 | — |
| *Cocos Nucifera* Oil | 100 | 1.0 | 1.0 | 1.0 | 1.0 |
| Guar Hydroxypropyl Trimonium Chloride | 100 | 0.2 | 0.2 | 0.2 | 0.2 |
| Parfum | 100% | 0.8 | 0.8 | 0.8 | 0.8 |
| DMDM Hydantoin and 3-iodo-2propylnylbutyl carbamate | 50% | 0.2 | 0.2 | 0.2 | 0.2 |
| Sodium chloride | 100% | Visc. | Visc. | Visc. | Visc. |
| Aqua | | q.s. to 100 | q.s. to 100 | q.s. to 100 | q.s. to 100 |

Process 1

At least 7% of water was heated to about 80° C. in a side pot. To this, was added the fatty alcohol, light oil, secondary anionic (Sodium Cetylstearyl sulphate) and cationic (Behenyl Trimethyl Ammonium Chloride) surfactants, with high speed stirring. When uniform dispersion obtained, this mixture was cooled down to about 45° C. with the same speed stirring. This mixture was then added in the diluted primary surfactant solution (Sodium Laureth Sulphate) following by remaining components with moderate speed stirring.

Process 2

At least 7% of water was heated to about 80° C. in a side pot. To this, was added the fatty alcohol, secondary anionic (Sodium Cetylstearyl sulphate) and cationic (Behenyl Trimethyl Ammonium Chloride) surfactants, with high speed stirring. When uniform dispersion obtained, this mixture was cooled down to about 45° C. with the same speed stirring. This mixture was then added in the diluted primary surfactant solution (Sodium Laureth Sulphate) following by remaining components with moderate speed stirring, add light oil after adding salt.

Rheology Data

| Component | % ad | Base1 | Base2 | Base3 | Base4 | Base5 | Base6 | Base7 | Base8 |
| --- | --- | --- | --- | --- | --- | --- | --- | --- | --- |
| Sodium Laureth Sulphate | 70 | 17.14 | 17.14 | 17.14 | 17.14 | 17.14 | 17.14 | 17.14 | 17.14 |
| Cocoamidopropyl Betaine | 30 | 5.33 | 5.33 | 5.33 | 5.33 | 5.33 | 5.33 | 5.33 | 5.33 |
| Carbomer | 100 | — | 0.4 | — | — | 0.4 | 0.4 | — | 0.4 |
| Glycol Distearate | 35 | — | — | 4.0 | — | — | 4.0 | 4.0 | 4.0 |
| Sodium Cetylstearyl sulphate | 100 | — | — | — | 0.6 | 0.6 | — | 0.6 | 0.6 |
| Cetostearyl Alcohol | 100 | — | — | — | 1.0 | 1.0 | — | 1.0 | 1.0 |
| Behenyl Trimethyl Ammonium Chloride | 77.5 | — | — | — | 0.06 | 0.06 | — | 0.06 | 0.06 |
| Guar Hydroxypropyl Trimonium Chloride | 100 | 0.2 | 0.2 | 0.2 | 0.2 | 0.2 | 0.2 | 0.2 | 0.2 |
| Sodium chloride | 100% | 0.8 | 0.8 | 0.8 | 0.8 | 0.8 | 0.8 | 0.8 | 0.8 |
| Aqua | | q.s. to 100 | q.s. to 100 | q.s. to 100 | q.s. to 100 | q.s. to 100 | q.s. to 100 | q.s. to 100 | q.s. to 100 |

| | Viscosity at 0.1 Pa (Pa · s) | Relaxation Time (s) | |
| --- | --- | --- | --- |
| Base1 | 1.8 | 0.006 | Base |
| Base2 | 9.3 | 0.025 | Base + Carbopol |
| Base3 | 3.5 | 0.020 | Base + EGDS |
| Base4 | 5.5 | 0.050 | Base + ACG |
| Base5 | 56.5 | 0.159 | Base + Car + ACG |
| Base6 | 15.4 | 0.040 | Base + Car + EGDS |
| Base7 | 18.5 | 0.126 | Base + ACG + EGDS |
| Base8 | 98.5 | 0.253 | Base + Car + ACG + EGDS |

Car: Carbomer
ACG: Anionic charged Cationic Gel network
EGDS: Ethylene Glycol Distearate

The invention claimed is:

1. Conditioning shampoo composition with an oil selected from polyalphaolefin oils, ester oils, triglyceride oils, hydrocarbon oils and mixtures thereof dispersed therein, the composition comprising from 1-26% by wt. of a cleansing phase comprising an anionic surfactant, a conditioning gel network, a polymeric suspending agent and a cationic deposition polymer, wherein said conditioning gel network comprises (1) an anionic surfactant having from 16 to 22 carbons: (2) a fatty material selected from the group consisting of fatty alcohols, fatty esters, fatty acids, fatty amides and mixtures thereof; and (3) a cationic surfactant having the formula $N^+(R^1)(R^2)(R^3)(R^4)$, wherein $R^1$, $R^2$, $R^3$ and $R^4$ are independently $C_{16}$ to $C_{30}$ alkyl or benzyl wherein the anionic and cationic surfactants in the gel network contain within 4 carbons of one another, wherein the anionic surfactant of the gel network provides overall anionic charge to the gel network or no overall charge; and wherein anionic surfactant and fatty material of the gel network are within 4 carbons.

2. Composition according to claim 1 wherein the conditioning gel network comprises a fatty material selected from fatty alcohols, fatty esters, fatty acids and fatty amides.

3. Composition according to claim 2 wherein the fatty material is straight chain or branched and has from 14 to 30 carbons.

4. Composition according to claim 1 wherein the oil has a viscosity of from 0.1 to 500 centipoises measures at 30° C. on a Brookfield viscometer with spindle RV5 and 20 rpm.

5. Composition according to claim 1 comprising a cationic polymer.

6. Composition according to claim 1 comprising a silicone.

* * * * *